United States Patent [19]

Rivers, Jr. et al.

[11] 4,132,535

[45] Jan. 2, 1979

[54] PROCESS FOR INJECTING LIQUID IN MOVING NATURAL GAS STREAMS

[75] Inventors: Jacob B. Rivers, Jr., Oklahoma City, Okla.; Harry T. Budke, Jr., Overland Park, Kans.

[73] Assignee: Western Chemical Company, North Kansas City, Mo.

[21] Appl. No.: 742,443

[22] Filed: Nov. 17, 1976

[51] Int. Cl.$^2$ ............................................. B01D 51/00
[52] U.S. Cl. ............................................. 55/23; 55/45; 55/84; 137/13; 208/48 AA; 252/358
[58] Field of Search ............. 55/29, 30, 23, 40, 43–46, 55/88, 87, 84; 526/265; 208/340, 47, 48 AA; 137/13; 252/358, 360–363

[56] References Cited

U.S. PATENT DOCUMENTS

| | | | |
|---|---|---|---|
| 2,151,248 | 3/1939 | Vaughan | 55/45 |
| 2,663,669 | 12/1953 | Barnes | 208/340 |
| 2,690,814 | 10/1954 | Reid | 55/32 |
| 2,771,462 | 11/1956 | Shen et al. | 252/358 |
| 2,828,270 | 3/1958 | Murata | 526/265 |
| 3,198,774 | 8/1965 | Huxtable | 526/265 |
| 3,474,596 | 10/1969 | Scott et al. | 55/45 |
| 3,515,575 | 6/1970 | Arnold | 252/358 |
| 3,770,712 | 11/1973 | Schwab | 526/265 |

*Primary Examiner*—Bernard Nozick
*Attorney, Agent, or Firm*—Schmidt, Johnson, Hovey & Williams

[57] ABSTRACT

A simplified, low-cost method of treating pressurized, moving natural gas streams in order to control problems created by entrained water in the gas is provided which facilitates downstream treatment of the gas and increases product yields by lessening the formation of oil and water emulsions and hydrates which can coat and clog processing equipment, while also minimizing corrosion of the latter. The method involves introduction of an agent into the moving gas stream which includes a polymer having recurring quaternized pyridinium groups therein for controlling the emulsion, hydrate and corrosion problems; the method is especially effective when the entrained water contains surfactants, detergents, soaps, and the like. In preferred forms a low molecular weight copolymer of styrene and 2-vinyl pyridine dispersed in water is atomized into the gas stream adjacent cooling and scrubbing stations. The present method finds particular utility in connection with natural gas products plants, although other types of gas-processing facilities can also be served.

8 Claims, 1 Drawing Figure

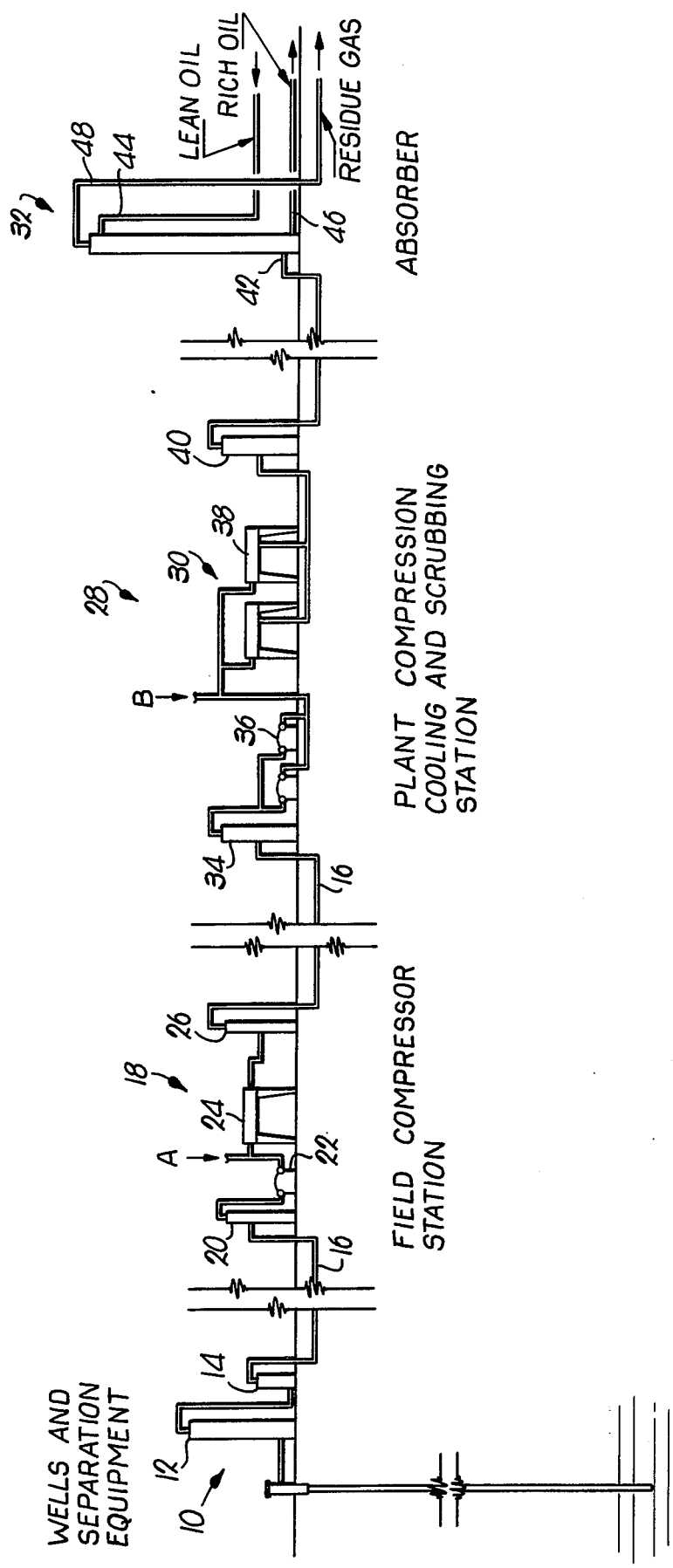

PROCESS FOR INJECTING LIQUID IN MOVING NATURAL GAS STREAMS

The present invention is concerned with a method for treating natural gas streams in order to facilitate control of entrained water therein which can cause severe processing problems. More particularly, the invention is concerned with a method wherein an agent including a quaternized pyridinium polymer is introduced into a gas stream for controlling the entrained water and surfactants therein so as to alleviate the troublesome problems of emulsion formation in the processing equipment, corrosion due to acids formed in the entrained water, and the buildup of crystalline hydrates in the gas line.

In general, the treatment and processing of natural gas obtained from oil production operations is well known. One long-established procedure involves the production of so-called natural gasoline and gas products from well-derived gas. This involves transporting large volumes of natural gas from the well head through pipeline provided for this purpose to a gas treatment facility. At this location for absorbtion-type plants the gas is generally run through an absorber tower in countercurrent relationship to oil which absorbs a fraction of the hydrocarbons in the gas stream. This "rich oil" is then distilled to yield gasoline and other hydrocarbon fractions such as butane, propane, ethane, etc., whereupon the oil can be recycled as "lean oil" back to the absorber tower.

It is also well known that water in particulate form becomes entrained in the gas stream as it leaves the well head. The quantity of water in a gas stream can vary widely from day to day and from well to well. For example, excess entrained water can cause the formation of emulsions with the hydrocarbons in the gas stream and the absorption oil passing through the absorber. These emulsions, which may be either of the water in oil or oil in water variety, can become very viscous and gelatinous in character and partly fill any equipment through which the gas stream passes such as demister equipment in the scrubbers, and hence impede gas flow. In actual practice, gelatinous emulsions have been known to literally fill the absorber bottom, flash tanks and primary vents of absorption-type natural gasoline plants, and thereby curtail gasoline production.

Another common problem stemming from the inability to control entrained water particles in natural gas streams is that of corrosion of pipeline and plant equipment. In this connection, the entrained water particles oftentimes also contain quantities of $H_2S$ and $CO_2$, and these in turn can cause severe corrosion problems. This can occur in the still of a natural gasoline plant, when the still is operated at a temperature below the dew point, as well as in the dephlegmators, absorbers and points of heat transfer therein such as lean oil-rich oil heat exchangers. These gases in the entrained water, which if not controlled, enter these components and can form sulfur based acids and carbonic acid which in turn corrosively attack the plant equipment.

Finally, it has long been recognized that entrained water can cause the formation of crystalline hydrates which clog gas pipelines. Such hydrates are formed under conditions of low temperature and high pressure, and in the pressure of free water. The pipeline conditions of temperature and pressure are essentially fixed, and accordingly hydrate control depends upon controlling the entrained water. Water control in connection with this specific problem is accomplished by water absorption techniques and refrigeration; however, both of these expedients involve high capital and operational costs. Injection of water absorbants such as glycol and methanol are also used with partial success.

The problems created by excessive entrained water in natural gas streams are thus well known and documented. Prior control techniques include the use of conventional knock-outs and inertial separators (scrubbers) which attempt to centrifugally separate the water particles from the gas stream by taking advantage of the greater density of the former. In addition, it has been known to inject various substances such as water absorbants (e.g., glycols) into natural gas streams. See, e.g., U.S. Pat. Nos. 3,633,342; 3,386,712; 3,608,274; 1,977,101; 2,046,500; 2,083,802; 2,207,774; 3,559,377; 3,704,570 and 3,803,805.

In recent years however, a number of gas processors have experienced emulsion and like problems which far exceed those of the past. This quite naturally has perplexed the operators of gas pipelines and processing plants, since for no apparent reason emulsion, corrosion and hydrate problems have multiplied to a point where conventional techniques of inertial separation and the like are no longer adequate. Of course, production at affected gas plants has been measurably curtailed because of the inability to control entrained water, and accordingly many efforts have been made to resolve this problem.

Another relatively recent development in the oil and gas industry is the large increase in the use of work-over techniques involving surfactants. That is, surfactants such as soaps (e.g., sodium lauryl sulfate) are now regularly injected into formations as an aid in oil and gas recovery. Such surfactants have proven to be valuable in increasing production from old, low-yield wells. However, it has unexpectedly been found that relatively large amounts of these surfactants can become entrained in the natural gas streams leaving the well head, and that the surfactants can remain in the streams even during final processing thereof at locations many miles from the well. It is also believed that these surfactants are a prime causative factor in the relatively recent increase in emulsion problems and the like, and accordingly control of surfactants and surfactant-laden water is necessary.

It is therefore the most important object of the present invention to provide an easy, inexpensive method for effectively controlling the entrained water in modern-day natural gas streams, and especially those having relatively high surfactant levels, to thereby alleviate the problems of emulsion and hydrate formation, and corrosion of gas pipelines and processing equipment.

As a corollary to the foregoing, another aim of the invention is to provide a method wherein an agent which includes a polymer having recurring quaternized pyridinium groups therein is introduced into a pressurized natural gas stream in order to control the entrained water problem and allow separation thereof using conventional, in-place equipment; the agent is advantageously injected into the gas stream at a point along the conduit and in an amount for effectively controlling the problems associated with excessive entrained water.

Another object of the invention is to provide a method wherein a dilute, aqueous dispersion including a copolymer of styrene and 2-vinyl pyridine having a molecular weight of 2,000 to 3,000 is injected in atomized form into a natural gas stream in an amount such that at least 0.002 lbs. (preferably from about 0.002 to 0.2 lbs.) of the copolymer is introduced per million cubic feet of the gas passing the introduction point.

The single FIGURE is a schematic, fragmentary view of an oil well, the gas transmission apparatus associated therewith, and a portion of an absorption-type natural gasoline plant.

Turning now to the FIGURE, a schematically represented oil well 10 is illustrated, along with conventional well head apparatus including a heater-treater 12 and knock-out 14. Heater-treater 12 is operable to elevate the temperature of crude oil recovered from well 10 and facilitate gas separation therefrom; this unit also, in conjunction with knock-out 14, removes a portion of the water and other liquids from the gas. An underground gas transmission conduit 16 is coupled to the output side of knock-out 14, and may extend for many miles towards downstream gas processing equipment. A plurality of midstream or field compressor stations 18 are provided along the length of conduit 16 and in general include an inlet scrubber 20, one or more compressors 22, heat exchangers or cooler 24, and appropriate high stage scrubbing equipment 26. The purpose of the field compressor station 18 is to remove a certain amount of the entrained water particles and distillate in the moving gas stream, and to cool and compress the latter up to a level of, for example, 300 p.s.i.

A portion of a natural gasoline plant 28 of the absorption variety is illustrated at the delivery end of transmission conduit 16. Such a plant normally includes a plant compression, cooling and scrubbing station 30, and an absorber tower 32. Station 30 has an inlet scrubber 34, a plurality of compressor 36, and final scrubber equipment 40. Again, the purpose of station 30 is to compress the natural gas and lower the temperature thereof prior to entrance into absorber tower 32.

Tower 32 is of the conventional tray and bubble cap variety and includes a lowermost gas inlet 42 and an upper lean oil inlet 44. The lean oil and natural gas are countercurrently contacted within absorber 32 in order that the lean oil can absorb a fraction of the hydrocarbons of natural gas which are recoverable as liquids. The rich oil resulting from this absorbtion process is passed through line 46 to appropriate downstream distillation and collection apparatus (not shown) which is used to recover the absorbed gasoline fractions such as butane, propane, etc., whereupon this oil in lean form is recycled back to the absorber tower. The unabsorbed gas passing through absorber 32 leaves the latter via lie 48 as residue gas and is then usable for residue sales.

It is to be understood that the foregoing description refers to conventional gas recovery and processing apparatus, and that the present invention is in no way limited to the type or specifics of the described structure. However, the invention does find particular utility in recovery and processing equipment of this type, and for purposes of illustration and clarity will be described in connection therewith.

As indicated above, in recent years there has been a tremendous increase in problems associated with formation of oil and water emulsions (i.e., either oil-in-water or water-in-oil) in gas processing equipment. For example, in the case of natural gasoline plants of the type described, severe emulsion problems have been noted in the absorber bottoms and the downstream equipment such as dephlegmators. In addition, extremely viscous gelatinous or "pudding-like" emulsions have also been noted on inlet gas scrubbers leading to the absorber and on equipment associated with absorption oil flow. These emulsions can create severe cleanup problems and limit recoverable liquid yields since they interfere with clean absorption and separation of the liquids.

While it has long been recognized that emulsion problems of this type (as well as problems associated with hydrate formation and corrosion) are principally due to excess entrained water in the natural gas stream, the magnitude of the relatively recent emulsion problems has defied explanation. However, it has now been determined that relatively large quantities of surfactants used during work-over techniques and the like can become entrained in the gas stream along with water, and this is believed to be the principal cause of modern-day emulsion and entrainment problems.

In this connection, it has been known in the past to cause coalescence of fine particulate water (as in a fog) by adding surfactants or polyelectrolytes to the system, and therefore the presence of surfactants in the gas stream could predictably have the effect of coalescing the entrained water and thereby facilitating separation thereof. See U.S. Pat. Nos. 2,895,679; 3,608,810; 3,608,820; 3,534,906; 3,888,641; 2,835,530 and 3,559,377. However, under the dynamic conditions experienced in natural gas pipelines and treating equipment, the presence of excess surfactants has unexpectedly proven troublesome.

In keeping with the present invention, it has been discovered that certain agents can be introduced into a moving, pressurized natural gas stream in order to control the entrained water and surfactant problem and thereby alleviate the problems discussed above. In particular, it has been found that introduction of an agent into the gas stream which includes a polymer having recurring quaternized pyridinium groups therein is effective for these purposes. In preferred forms, the agent is introduced by injection thereof into the stream in atomized form using conventional apparatus, in order to effect the most rapid and complete contact with the gas stream.

In actual practice, the preferred agent comprises a copolymer of an alkene-substitute pyridinium group and an alkene-substituted benzene group; the most preferred agent is a quaternized copolymer of styrene and 2-vinyl pyridine having a molecular weight of from about 2,000 to 3,000 which is dispersed in water. This preferred agent is advantageously employed in a quantity such that at least about 0.002 lbs. of the copolymer is introduced into the gas stream per million cubic feet of natural gas passing the injection point; most preferably the dosage level should be from about 0.002 to 0.2 lbs. per million cubic feet of gas. In dilute aqueous solution (4% by weight), the preferred agent is an amber liquid having a specific gravity of 0.995 (60° F.), a pH of about 8.6, and a flash point above 212° F. This preferred agent is known and has heretofore been used as an oil coalescent for industrial waste water clarification, and as a coagulant aid for oily solids.

Although the actual injection point can vary widely in a given system or between separate systems, in general the injection point should be selected so the natural gas passing the same is under a pressure of from about 150 to 600 p.s.i. and is moving at a rate of from about 5 to 650 feet per second. Referring again to the FIGURE, two particularly preferred injection points are illustrated. Point A is at one or more of the field compressor stations prior to cooling and final scrubbing of the gas, but subsequent to compression thereof. Similarly, Point B is located at the plant compression station and again the agent is introduced prior to cooling and scrubbing and before entrance into the absorption system. However, other specific injection points can be chosen throughout the gas transmission and processing system without departing from the spirit and scope of the invention.

The mechanism by which the agents of the invention serve to control the problems noted above is not fully understood. However, the following possible explanation is presented for purposes of completeness, although the invention is in no way bound to any specific explanation or operational theory.

It is hypothesized that the agents hereof may operate at least in part by increasing the surface tension of the entrained water particles. In this way the particles may be rendered more resistant to break up as they travel through the pipeline and processing equipment, to thereby remain susceptible to inertial or centrifugal separation. The presence of the well-derived surfactants in the gas stream is believed to lower the surface tension of the particles and thereby make them more liable to break up into very small particles during transmission and processing of the gas. This in turn would make it difficult to separate the fine particles and account for the excess water and emulsions present in the processing equipment. Thus, if the agents hereof do indeed raise the surface tension of the entrained particles, the integrity of the latter and resistance to break up would be enhanced.

The following Example is presented to illustrate the beneficial effects of the invention, but nothing therein is to be construed as a limitation on the invention.

EXAMPLE

In order to demonstrate the effect on gasoline production through the use of the present invention, the following example is presented.

Specifically, the incoming natural gas streams serving two separate conventional natural gasoline plants (hereinafter referred to as "Plant A" and "Plant B", respectively) were treated with the preferred agent of the invention, i.e., quaternized copolymer of styrene and 2-vinyl pyridine having a molecular weight of from about 2,000 to 3,000. In each case the plants had experienced the buildup of sludge in the absorber water and elsewhere, indicating the presence of unacceptably high oil-water emulsions. In addition, the gasoline production from the plants was below optimum.

In the case of Plant A, varying quantities of gas were handled (from about 4 to 5.5 million cubic feet) per day during the test period. During one Period, (Day 1 through Day 9, inclusive) no additive was added, and the average gasoline production was 7.733 gallons of gasoline per thousand cubic feet of treated gas. During the second period (Day 10 through Day 45, inclusive), the agent of the invention was added at a daily rate of 0.332 lbs. In all instances the agent was added by diluting the agent in water and atomizing the diluted product into the incoming gas stream by conventional means. The injection point was in the plant compression, cooling and scrubbing station just prior to cooling and scrubbing. The gasoline production rates during this second period averaged 8.561 gallons of gasoline per thousand cubic feet of gas processed, or an increase of 11% over Period 1. At the end of Day 45, introduction of the agent was discontinued and production continued without benefit thereof. During this last period (Day 46 through 50) gasoline production fell to an average of 8.423 gallons gasoline per thousand cubic feet of processed gas.

It is to be understood that gasoline production in an absorption-type gasoline plant can change from day to day as a result of a variance in many process and environmental conditions. However, the results of this test clearly demonstrate that average gasoline production is raised during use of the agent, although the precise amount of production increase attributable solely to the agent is difficult if not impossible to determine.

The following table sets forth the data collected during the above test:

TABLE I

PLANT A

| Day | Gasoline (Gallons) | Incoming Gas Processed MM Ft$^3$ | Gallons Gasoline Per M Ft$^3$ | Treatment Periods |
|---|---|---|---|---|
| 1 | 41015 | 5.300 | 7.739 | 1 |
| 2 | 41198 | 5.380 | 7.658 | 1 |
| 3 | 42559 | 5.452 | 7.806 | 1 |
| 4 | 42446 | 5.295 | 8.016 | 1 |
| 5 | 40282 | 5.275 | 7.636 | 1 |
| 6 | 40417 | 5.320 | 7.597 | 1 |
| 7 | 40691 | 5.411 | 7.520 | 1 |
| 8 | 42015 | 5.347 | 7.858 | 1 |
| 9 | 41465 | 5.339 | 7.766 | 1 |
| 10 | 40146 | 5.392 | 7.445 | 2 |
| 11 | 42995 | 5.083 | 8.459 | 2 |
| 12 | 41839 | 4.860 | 8.609 | 2 |
| 13 | 42236 | 5.228 | 8.079 | 2 |
| 14 | 41287 | 5.228 | 7.897 | 2 |
| 15 | 44046 | 5.009 | 8.793 | 2 |
| 16 | 40793 | 4.953 | 8.236 | 2 |
| 17 | 42018 | 5.346 | 7.860 | 2 |
| 18 | 42457 | 5.275 | 7.992 | 2 |
| 19 | 44532 | 5.070 | 8.783 | 2 |
| 20 | 44736 | 5.063 | 8.836 | 2 |
| 21 | 42583 | 5.045 | 8.441 | 2 |
| 22 | 41504 | 5.164 | 8.041 | 2 |
| 23 | 44074 | 5.148 | 8.561 | 2 |
| 24 | 40781 | 5.259 | 7.755 | 2 |
| 25 | 42920 | 5.300 | 8.098 | 2 |
| 26 | 45757 | 5.174 | 8.844 | 2 |
| 27 | 44492 | 5.228 | 8.510 | 2 |
| 28 | 45408 | 5.403 | 8.404 | 2 |
| 29 | 45868 | 5.155 | 8.899 | 2 |
| 30 | 43199 | 5.257 | 8.217 | 2 |
| 31 | 41157 | 4.350 | 9.461 | 2 |
| 32 | 40801 | 4.317 | 9.451 | 2 |
| 33 | 38799 | 4.402 | 8.814 | 2 |
| 34 | 39801 | 4.251 | 9.363 | 2 |
| 35 | 35957 | 4.134 | 8.699 | 2 |
| 36 | 38990 | 4.128 | 9.445 | 2 |
| 37 | 38402 | 4.143 | 9.269 | 2 |
| 38 | 40797 | 4.858 | 8.398 | 2 |
| 39 | 41920 | 5.023 | 8.346 | 2 |
| 40 | 42729 | 4.752 | 8.992 | 2 |
| 41 | 41486 | 4.914 | 8.442 | 2 |
| 42 | 43029 | 4.928 | 8.732 | 2 |
| 43 | 43056 | 4.924 | 8.744 | 2 |
| 44 | 43140 | 5.012 | 8.607 | 2 |
| 45 | 43492 | 5.008 | 8.685 | 2 |
| 46 | 43921 | 5.009 | 8.768 | 3 |
| 47 | 45635 | 5.359 | 8.516 | 3 |
| 48 | 44057 | 5.191 | 8.487 | 3 |
| 49 | 49361 | 5.143 | 7.848 | 3 |
| 50 | 43083 | 5.072 | 8.494 | 3 |

Plant B is also a natural or casinghead gasoline plant of larger capacity than Plant A. The test procedure in this case is essentially identical to that described above in connection with Plant A. The dosage rate of the preferred agent was 0.332 lbs. per day, again introduced as an aqueous diluted spray atomized into the gas stream prior to plant cooling and scrubbing. During Period 1 (Day 1 through Day 18, inclusive), the average gasoline production was 2.937 gal./M ft.$^3$ of gas processed; during Period 2 (Day 19–41, inclusive) average production was 3.081 gas/M ft.$^3$, or an increase of about 5%; and during Period 3, average production fell to 3.006 gal./M ft.$^3$. Again the same trend as noted above in connection with Plant A was apparent in this test.

The data gathered during this test is set forth hereunder:

TABLE II

| | | PLANT B | | |
|---|---|---|---|---|
| Day | Gasoline (Gallons) | Incoming Gas Processed MM Ft$^3$ | Gallons Gasoline Per M Ft$^3$ | Treatment Periods |
| 1 | 197,834 | 68.676 | 2.881 | 1 |
| 2 | 197,834 | 69.338 | 2.853 | 1 |
| 3 | 199,334 | 68.783 | 2.898 | 1 |
| 4 | 197,298 | 67.583 | 2.919 | 1 |
| 5 | 202,299 | 68.459 | 2.956 | 1 |
| 6 | 203,520 | 68.981 | 2.950 | 1 |
| 7 | 194,944 | 68.669 | 2.839 | 1 |
| 8 | 197,866 | 68.232 | 2.900 | 1 |
| 9 | 199,895 | 69.050 | 2.895 | 1 |
| 10 | 191,137 | 68.787 | 2.779 | 1 |
| 11 | 202,505 | 68.992 | 2.935 | 1 |
| 12 | 210,350 | 69.286 | 3.036 | 1 |
| 13 | 209,431 | 70.535 | 2.969 | 1 |
| 14 | 198,701 | 69.086 | 2.867 | 1 |
| 15 | 209,139 | 67.577 | 3.095 | 1 |
| 16 | 204,292 | 38.239 | 2.994 | 1 |
| 17 | 201.013 | 68.666 | 2.927 | 1 |
| 18 | 205,782 | 68.660 | 2.977 | 1 |
| 19 | 210,767 | 67.441 | 3.125 | 2 |
| 20 | 212,155 | 67.856 | 3.127 | 2 |
| 21 | 207,227 | 66.797 | 3.102 | 2 |
| 22 | 207,868 | 67.366 | 3.086 | 2 |
| 23 | 210,188 | 67.347 | 3.121 | 2 |
| 24 | 200,607 | 66.196 | 3.031 | 2 |
| 25 | 211,131 | 67.816 | 3.113 | 2 |
| 26 | 217,026 | 66.408 | 3.268 | 2 |
| 27 | 217,944 | 67.022 | 3.252 | 2 |
| 28 | 212,507 | 66.666 | 3.188 | 2 |
| 29 | 213,667 | 65.572 | 3.259 | 2 |
| 30 | 207,204 | 65.069 | 3.184 | 2 |
| 31 | 211,057 | 67.295 | 3.136 | 2 |
| 32 | 215,116 | 67.391 | 3.192 | 2 |
| 33 | 213,008 | 69.929 | 3.046 | 2 |
| 34 | 214,391 | 70.150 | 3.056 | 2 |
| 35 | 200,240 | 70.169 | 2.854 | 2 |
| 36 | 209,309 | 70.006 | 2.990 | 2 |
| 37 | 206,430 | 69.662 | 2.963 | 2 |
| 38 | 207,926 | 69.619 | 2.987 | 2 |
| 39 | 205,422 | 70.216 | 2.926 | 2 |
| 40 | 208,737 | 69.395 | 3.008 | 2 |
| 41 | 202,329 | 69.788 | 2.899 | 2 |
| 42 | 199,029 | 68.448 | 2.908 | 3 |
| 43 | 199,603 | 69.263 | 2.882 | 3 |
| 44 | 201,181 | 69.030 | 2.914 | 3 |
| 45 | 201,325 | 67.041 | 3.003 | 3 |
| 46 | 203,520 | 67.438 | 3.018 | 3 |
| 47 | 211,057 | 68.404 | 3.085 | 3 |
| 48 | 210,043 | 67.628 | 3.106 | 3 |
| 49 | 202,255 | 67.252 | 3.007 | 3 |
| 50 | 201,940 | 66.176 | 3.052 | 3 |
| 51 | 203,310 | 66.012 | 3.080 | 3 |

Having thus described the invention, what is claimed as new and desired to be secured by Letters Patent is:

1. A method for treating natural gas streams comprising the steps of:
   providing a moving gas stream traveling through a confining conduit, said gas stream principally comprising natural gas and having entrained products therein which include fine water particles and surfactant capable of forming emulsions with hydrocarbons in said stream; and
   injecting a liquid into said gas stream in atomized form, said liquid containing a copolymer of alkene-substituted quaternized pyridinium groups and alkene-substituted benzene groups for substantially preventing the formation of emulsions in downstream gas processing equipment, said agent being injected into said gas stream at a level of from about 0.002 to 0.2 lbs. of copolymer per million cubic feet of said gas passing said injection point.

2. The method as set forth in claim 1 wherein said gas stream is under pressure.

3. The method as set forth in claim 1 wherein said gas stream is moving at a rate of from about 5 to 650 ft/sec.

4. The method as set forth in claim 1 wherein said liquid is introduced into said stream prior to cooling and scrubbing of the gas.

5. The method as set forth in claim 1 wherein said liquid is introduced into said stream adjacent a field compressor station prior to cooling and scrubbing of the gas.

6. The method as set forth in claim 1 wherein said liquid is introduced into said stream adjacent a plant compression station prior to cooling and scrubbing of the gas.

7. The method as set forth in claim 1 wherein said liquid comprises an aqueous dispersion of a quaternized copolymer of styrene and 2-vinyl pyridine having a molecular weight of from about 2,000 to 3,000.

8. The method as set forth in claim 7 wherein said liquid is introduced in a quantity such that at least about 0.002 lbs. of said copolymer is introduced per million cubic feet of said gas passing said introduction point.

* * * * *